United States Patent [19]
Pièrre et al.

[11] Patent Number: 4,974,963
[45] Date of Patent: Dec. 4, 1990

[54] PORTABLE AND AUTONOMOUS INSTRUMENT FOR ANALYZING A GASEOUS COMPOSITION BY MEANS OF FLAME SPECTROPHOTOMETRY

[75] Inventors: Clausin Pièrre, Ville d'Avrey; Bleuse Patrick, Lequesnoy; Guene Gilles, Elancourt, all of France

[73] Assignee: Proengin, Saint Cyr L'Ecole, France

[21] Appl. No.: 279,598
[22] PCT Filed: Feb. 25, 1988
[86] PCT No.: PCT/FR88/00105
  § 371 Date: Oct. 31, 1988
  § 102(e) Date: Oct. 31, 1988
[87] PCT Pub. No.: WO88/06727
  PCT Pub. Date: Sep. 7, 1988

[30] Foreign Application Priority Data
  Mar. 2, 1987 [FR] France ............... 87 02762

[51] Int. Cl.⁵ .......................................... G01N 21/72
[52] U.S. Cl. ....................... 356/417; 356/315
[58] Field of Search .................. 356/315, 417

[56] References Cited
U.S. PATENT DOCUMENTS
3,791,743 2/1974 Cody et al. .................. 356/417
4,099,883 7/1978 Berger et al. ................ 356/417

Primary Examiner—F. L. Evans
Attorney, Agent, or Firm—William A. Drucker

[57] ABSTRACT

Instrument comprising a burner (22) provided with a window (221), on the axis of which is disposed a flame spectrophotometric device consisting of a focusing lens (222, 231), a chopper (223) introducing a number of optical filters (224) at the rate of one per characteristic line in the spectrum of the element under analysis, an optoelectronic cell (232) disposed within the focusing zone of said lens, a demodulation assembly for demodulating the electric signal emitted by said cell, and devices for amplifying and displaying the electric signal emitted by said assembly. Special provisions render the instrument portable and autonomous without detracting from its high precision.

35 Claims, 6 Drawing Sheets

PORTABLE AND AUTONOMOUS INSTRUMENT FOR ANALYZING A GASEOUS COMPOSITION BY MEANS OF FLAME SPECTROPHOTOMETRY

The invention relates to an apparatus for analysing a gaseous composition by flame spectrophotometry.

It relates more particularly, but not exclusively, to the construction of a portable apparatus of this kind which makes it possible to measure instantaneously, with direct reading, the proportion of gaseous elements contained in the ambient air, for example polluting elements or even war gas.

It is known generally that flame spectrophotometry is a method which consists in making a spectrographic analysis of the radiation produced by the flame of a gas mixture including the elements to be analyzed. This analysis may be made by isolating the characteristic radiations of the desired elements and measuring the intensity of these radiations photometrically. Through previous calibration of the apparatus on gaseous compositions of known concentration, it becomes possible to obtain the proportion of a desired element in a gaseous mixture, directly from this measurement of intensity.

Thus, in the case of analysing the ambient air, the flame is usually obtained by combustion, inside a burner of a constant flow rate hydrogen stream in the air flow to be analysed.

The invention relates more particularly to the construction of a self-contained portable analysis apparatus, however of high precision, based on this method.

Now, because of the nature of the elements used and, in particular, the hydrogen source, the means for regulating the flow rate which are associated therewith, the burner, the optical system used for the spectrographic analysis, the optoelectronic measurement circuits and the source of electric energy required for operating the whole, such a construction seems at first hand difficult to conceive.

To solve this problem, the invention proposes first of all, for the hydrogen production, using a hydrogen accumulator of the type in which the release of hydrogen is obtained by the heating of elements such as hydrogen impregnated lanthanum-nickel granules contained in a small volume interchangeable cartridge.

This solution which makes it possible to overcome the problems of size and weight of the hydrogen source involves on the contrary for heating the lanthanum granules to the prescribed temperature, a relatively high electric power consumption requiring, in order to maintain sufficient autonomy, relatively bulky and heavy electric power sources. In other words, the advantage obtained by adopting the above hydrogen generator is offset by the size of the electric source which it requires.

Now, it has proved that the hydrogen flow which is required for ensuring operation of the analysis device is relatively small and does not require continuous heating, of constant power, of the hydrogen generator.

On the basis of this discovery the invention proposes, in order to limit the heating power to strictly what is necessary making the heating device dependent on the hydrogen pressure reigning upstream of the regulator which supplies the burner with hydrogen at a constant flow rate. In fact, the part of the hydrogen circuit situated upstream of this regulator forms a buffer volume in which the hydrogen pressure may vary above a threshold value in a pressure range appropriate to that required by the regulator so as to maintain the hydrogen flow constant. The control used will then serve for maintaining the hydrogen pressure reigning inside said volume within said pressure range by continuously or discontinuously adjusting the electric power applied to the heating device.

Advantageously, the flow rate regulation device may comprise, in series, a membrane pressure reducer and a flow regulator. In this case, pressure detection may be accomplished by detecting the position of the membrane of the pressure reducer.

In an advantageous embodiment of the invention said flow regulator device comprises a hollow preferably cylindrical body with two opposite coaxial orifices, namely an access orifice for connecting to the hydrogen accumulator and an outlet orifice connected to the burner and an internal dividing wall, perpendicular to the axis of said orifices, which defines two chambers inside the body, one of which, situated on the access orifice side, forms the chamber of the pressure reducer and the other, situated on the outlet orifice side, forms the chamber of the flow regulator, communication between these chambers taking place through a bore provided in the dividing wall, coaxial to said orifices.

The access orifice is equipped with a needle having an axial channel and whose head, which projects inside the chamber of the flow regulator, cooperates with a valve carried by a support structure secured to a resiliently deformable membrane which is sealingly mounted on the body and on the needle and extends in a plane perpendicular to the axis of said orifices and divides the chamber of the flow regulator into two cavities hermetically isolated from each other and the first of which communicates with the atmosphere and the second, fed with hydrogen through the channel of the needle, communicates with the chamber of the flow regulator through the bore in said dividing wall. Thus, under the effect of the hydrogen pressure injected into the second cavity, the membrane is deformed and tends to apply the valve on the head of the needle and, consequently to close the channel.

Similarly, said outlet orifice is equipped with a needle having an axial channel whose head cooperates with a valve carried by a resiliently deformable membrane which divides the regulation chamber into two cavities hermetically isolated from each other, one of which communicates with the central bore in said dividing wall and the other communicates with the channel of the outlet needle. Communication between these two cavities is then provided by a vacuum producing element preferably formed by a capillary passing through the membrane and one part at least of which extends radially into one of the two cavities.

According to a particularly advantageous characteristic of the above described flow regulator, the axial position of said two needles may be adjusted for example by means of screwing means provided in said inlet and outlet orifices. Thus particularly simple and readily accessible means are provided for adjusting the hydrogen flow.

As mentioned above, the analysis device of the invention includes a burner fed with a hydrogen flow at constant rate coming from the flow regulator and a flow of air to be analysed taken by means of a circulator. This burner has a window in the axis of which the flame spectrophotometry device is disposed which comprises successively:

an optical system for focusing the light radiation emitted by the flame which is developed inside the burner, a chopper including a plurality of optical filters, at the rate of at least one per characteristic spectral line of the desired element, as well as means for placing said filters successively in the previously focused light beam, an optoelectronic cell placed in the focusing zone of the focusing optics, an assembly for demodulating the electric signal delivered by said cell, this assembly comprising for each of said spectral lines and consequently, for each of said filters, a demodulator-separator driven in synchronism with the chopper so as to be made active only when the light beam from the focusing optics passes through a corresponding filter, and means for amplifying and displaying the electric signal delivered by said demodulator-separators.

Several embodiments of the invention will be described hereafter, by way of non limitative examples, with reference to the accompanying drawings in which.

Figure 1:
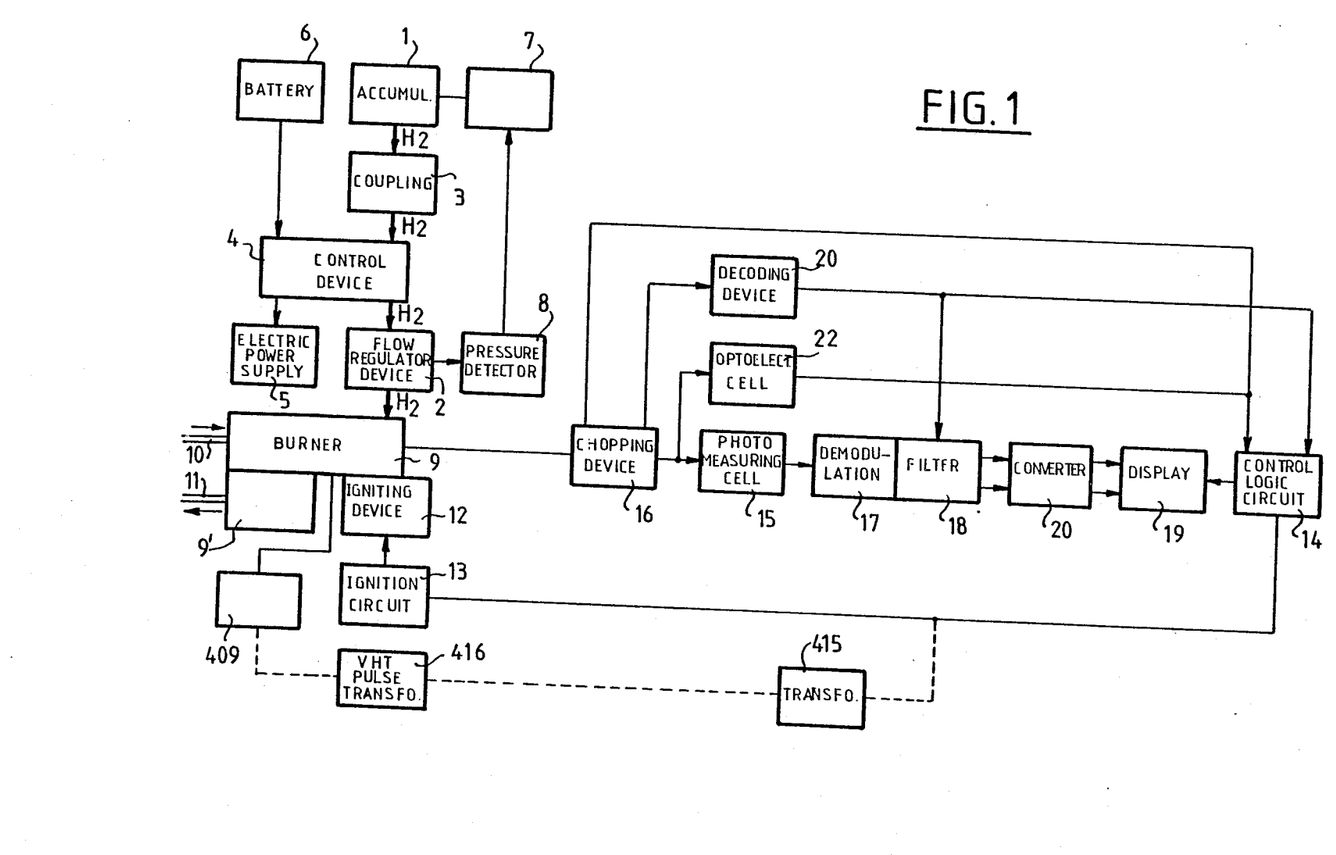
FIG. 1 is a block diagram of an analysis device in accordance with the invention.

In the example shown in FIG. 1, block 1 corresponds to the hydrogen accumulator which, as mentioned above, is in the form of a removable cartridge of small dimensions containing lanthanum-nickel granules for storing the hydrogen. This hydrogen accumulator is coupled to a flow regulator device 2, preferably coaxial, by means of a coupling device (block 3) associated with a control device (block 4) which controls both the hydrogen supply for the flow regulator device and the electric power supply (block 5) for the whole of the analysis device from a source (block 6), for example a battery of dry cells or accumulators.

The cartridge of the hydrogen accumulator is heated by heating means (block 7) whose heating power is regulated by a pressure detector (block 8) associated with the flow regulator device 2.

At the output of the flow regulator device 2, the hydrogen is injected into a burner 9 in which flows an air stream provided by an air suction circuit 10 and and discharge circuit 11. This burner is equipped with an optical device for processing the light radiation emitted by the flame resulting from the combustion of the hydrogen inside the burner and a device for igniting and maintaining the flame (block 12). This device is controlled by an ignition circuit (block 13), associated with a control logic circuit (block 14), as a function of the presence and of the brilliance of the flame.

The airflow inside the burner may advantageously be provided by a circulator (block 9') mounted directly on the body of burner 9 and thus avoiding the use of a connecting pipe which may be the seat of condensates. Advantageously, this circulator may be slaved to the intensity of the ultraviolet radiation detected by the cell. Furthermore, a detector, for example a flow detector for detecting malfunctioning of the circulator may be provided as well as a device for interrupting the flame ignition and maintenance circuit (block 12) when this detector emits a fault signal.

The optical processing device associated with the burner is designed so as to transmit, to a photoelectric measuring cell (block 15), the light radiation emitted by the flame, through a device for chopping and selectively filtering this radiation (block 16). As mentioned above, this chopping device comprises a plurality of optical filters, at the rate of at least one per spectral line desired, which are successively placed in the light beam produced by the optical processing device.

The electric signal produced by cell 15 is then transmitted to a demodulation assembly 17 comprising for each of the desired spectral lines, a demodulator and an appropriate filter 18. This demodulation assembly 17 is driven by a decoding device 20 for assigning to each demodulator/filter pair the signal delivered by cell 15 during filtering of the light beam by a corresponding filter.

Filters 18 of the demodulation assembly are connected by their respective outputs to a display device 19 through a converter 520. This display device is itself driven by the control logic circuit 14. Advantageously, this display device may be completed or replaced by a signalling system outputting a light or sound signal at a variable amplitude and/or frequency.

Besides the filters assigned to the desired spectral lines, the chopping device may further comprise an ultraviolet filter associated with a corresponding optoelectronic cell 22, preferably separate from cell 15. This cell which delivers a signal representative of the presence of the light intensity of the flame is connected to the control logic circuit 14. Depending on the illumination condition of the flame, this circuit 14 may start up the ignition device and possibly correct the measurements displayed by the display device 19.

FIGS. 2 to 8 are embodiments of the main elements forming part of the previously described diagram.

Figure 2:
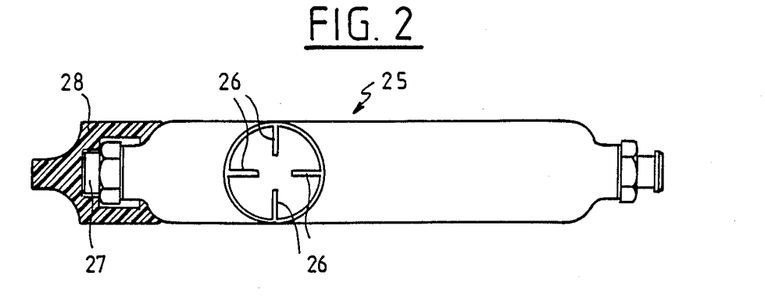
FIG. 2 is an axial section through a lanthanum-nickel cartridge usable in the device of the invention.

Thus, FIG. 2 shows a particularly advantageous embodiment of a removable lanthanum-nickel cartridge for storing the hydrogen.

It should be noted first of all in this connection that the cartridges of this kind used at the present time are formed of a generally cylindrical tubular body closed on one side by a bottom and having on the other a connecting end piece with a valve adapted to be urged in the opening direction at the time of connection, once this connection has been made. This tubular body serves for containing the lanthanum-nickel which is in the form of powder and is heated by external means for ensuring the required hydrogen production.

It has proved that such cartridges have a number of drawbacks.

Because of its low conductivity, the lanthanum-nickel powder takes a relatively long time to heat up under the effect of the heat released by the body, when the heating means are brought into service. This results in a relatively long response time and a mediocre quality of the control of the heating means.

Furthermore, during handling, the powder frequently becomes packed and forms, inside the body, a conglomerate which, when it is impregnated with the hydrogen, undergoes swelling which produces high stresses on the body which may even deform it.

Another drawback of these cartridges consists in the fact that, when accidental closure of the hydrogen circuit occurs, during a phase for heating the cartridge, there occurs a considerable rise of the hydrogen pressure creating a risk of explosion.

The solution illustrated in FIG. 2 overcomes all these drawbacks.

It comprises a body 25 having a plurality of radial fins 26 (seen in cross section) which extend axially throughout the inner volume of body 25 substantially over the whole of its length. These fins 26 then provide an improved heat transfer between the body and the powder, allowing a better homogeneity of the heating and ensure homogeneous distribution of the powder thus preventing the formation of a conglomerate.

Furthermore, the bottom of the cartridge includes an orifice closed by a stopper 27 (such for example as a breakage disk) which is ejected when the pressure inside the cartridge rises above a predetermined threshold.

It is clear that at the time of such ejection, the pressure inside the cartridge will be suddenly lowered and, at the same time, the lanthanum-nickel powder which undergoes cooling, will cease its hydrogen production.

The stopper may be protected by a cap 28 forming a handle which for example may serve for rotating the cartridge during its connection to the apparatus.

The heating of the above described cartridge may be achieved conventionally by means of a heating resistance network whose supply is controlled by a switch. However, this solution does not allow a proportional control of the heating to be obtained and adaptation to a wide range of supply voltages (such an adaptation would require the use of a multiplicity of resistors each corresponding to a voltage level).

Figure 3:
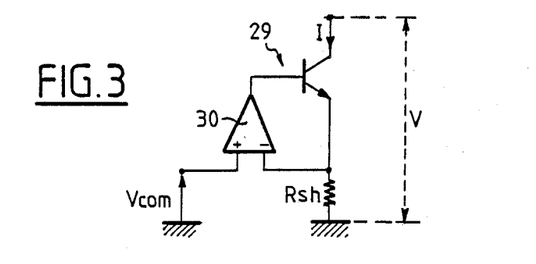
FIG. 3 shows one embodiment of a heating circuit which may be used for heating a lanthanum-nickel cartridge for producing hydrogen in a device such as the one shown in FIG. 1.

This is why the invention proposes using, in order to provide this heating, active components such as CMS transistors whose heating power P may be controlled by a control voltage, for example using the circuit shown in FIG. 3.

In this circuit, the collector-emitter junction of transistor 29 is connected to a voltage source V through a shunt resistor Rsh, in series in the emitter circuit. The base of this transistor 29 is connected to the output of an operational amplifier 30, whose inverter input is connected to the emitter of transistor 29 and whose forward input receives a control voltage $V_{com}$ The power P dissipated by the transistor is then by the form:

$$P = VI = \frac{V \times V_{com}}{Rsh}$$

The above described connection device is connected to a flow regulator device including, in series, a pressure reducer and a flow regulator properly speaking.

Figure 5:
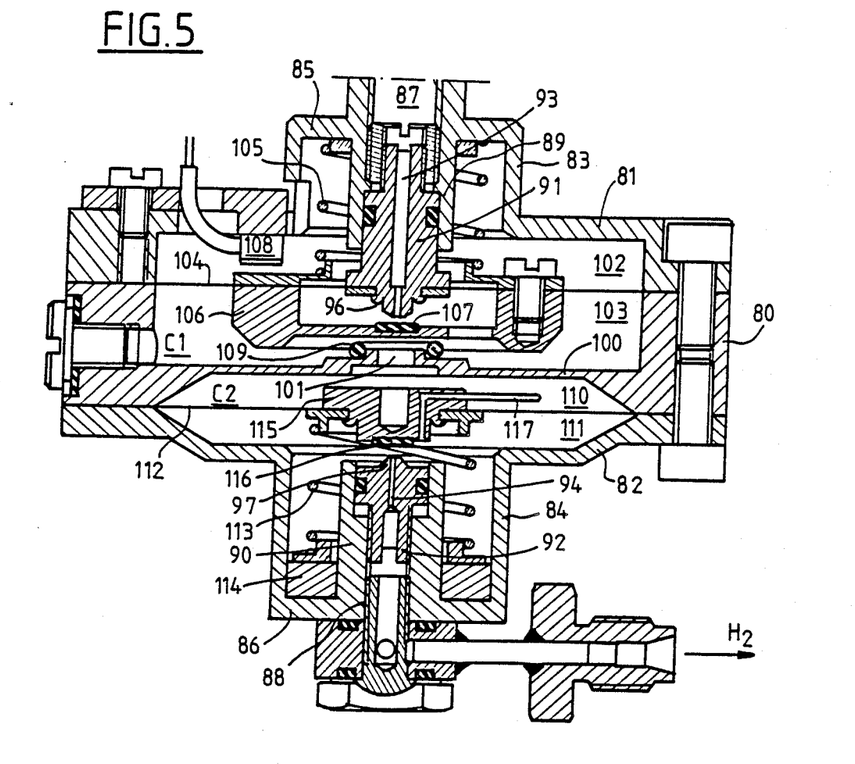
FIG. 5 is an axial section through a flow regulator device.

FIG. 5 shows one particularly advantageous embodiment of such a device in which the pressure reducer and the flow regulator are incorporated in the same case.

In this example, the case has a tubular body 80 of cylindrical section closed by two opposite casings 81, 82 each having, coaxial to said body 80, a cylindrical boss 83, 84 whose bottom 85, 86 has a coaxial orifice 87, 88 and a cylindrical sleeve 89, 90 which surrounds said orifice 87, 88 and extends inwardly of the case.

Sleeve 89 is intended to be connected to the connection device, whereas sleeve 90 is provided for connection to the burner. In each of these sleeves 89, 90 a needle 91, 92 is mounted which is axially adjustable in position and has an axial channel 93, 94 for the passage of the hydrogen. Furthermore, these two needles 91, 92 each have a head 96, 97 oriented inwardly of the case and projecting from the inner end of the corresponding sleeve 89, 90.

Body 80 includes a radial dividing wall 100 which divides the internal volume of the case into two compartments C1, C2 which communicate with each other through a central bore 101 provided in the dividing wall 100.

Compartment C1 is itself divided into two chambers 102, 103 by a flexible circular membrane 104 whose peripheral edge is clamped between the casing 81 and body 80 at the level of the junction between these two parts and thus provides sealing of this junction, and whose central part is sealingly fixed to the head 96 of needle 91. This membrane 104 is urged by a spring 105 which is engaged in the space between sleeve 89 and the cylindrical wall of boss 83 so as to bear against bottom 85. It includes a support piece 106 which extends into chamber 102 and is provided with a seal 107 intended to cooperate with the head 96 of needle 91 in the manner of a valve.

This pressure reducer operates then in the following way:

when the hydrogen pressure in chamber 103 is zero, membrane 104, which is pushed by spring 105, moves seal 107 away from the head 96 of the needle 91, so that the hydrogen arriving through channel 93 may penetrate freely into chamber 103.

when the pressure inside this chamber 103 rises, the membrane 104 tends to rise against the action of spring 105 until, from a given pressure, seal 107 is applied on head 96 and closes channel 93.

The movements of membrane 104 which are representative of the pressure which reigns in chamber 103 (chamber 102 communicating with the atmosphere) are detected by a distance detector 108 mounted in chamber 102, this detector 108 serving for controlling the heating power applied to the hydrogen accumulator.

Support piece 106 further comprises, on the side opposite seal 107 a flat surface intended to cooperate with an O seal 109, in the manner of a valve, so as to close orifice 101 when the pressure inside this chamber 103 drops below a predetermined threshold. This arrangement thus avoids any rise of air into the hydrogen circuit from the burner.

Compartment C2 is also divided into two chambers 110, 111 by a flexible circular membrane 112 whose peripheral edge is clamped between body 80 and casing 82, at the level of the junction of these two parts, and thus provides sealing of this junction.

This membrane 112 is urged by a spring 113 which is engaged in the space between sleeve 90 and the cylindrical wall of boss 84 so as to then to come to bear on a support piece 114 whose thickness is variable as a function of the temperature, which rests on bottom 86, this piece 114 thus providing a temperature compensation of the action of spring 113.

Membrane 112 comprises, in its central part, a rigid piece 115 having a seal 116 intended to cooperate with the head 97 of needle 92 in the manner of a valve so as to close channel 94 at least partially as a function of the pressure differential existing between the two chambers 110, 111 and thus to play the role of flow regulator. For this, the two chambers 110, 111 communicate together through a vacuum producing element which in this example consists of a capillary element 117 which passes through piece 115 and extends radially into chamber 110, the length of this element being adjusted to the flow rate it is desired to obtain. It is clear that with this structure the charge set by the valve (seal 116 - head 97) will vary as a function of the pressure differential (chamber 110/chamber 111) so as provide a constant flow rate regulation of the hydrogen flow in channel 94.

Figure 6:
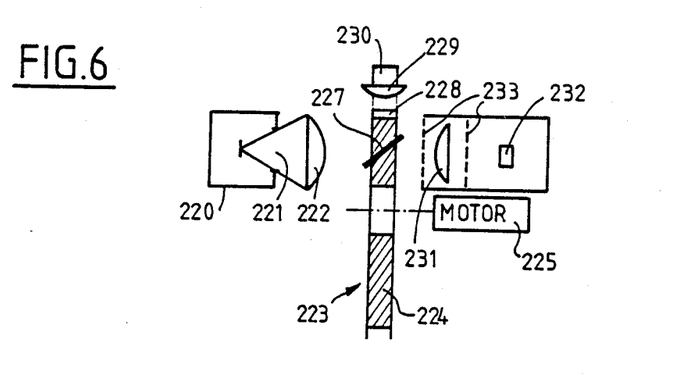
FIG. 6 is a schematical view of the burner and of the optics which is associated therewith.

FIG. 6 shows schematically a burner which may be used in the analysis device of the invention as well as the optics associated therewith.

This burner comprises more particularly a combustion chamber 220, for example cylindrical, in which are injected a flow of air coming from a circulation device not shown and a flow of hydrogen coming from the flow regulator device. This combustion chamber 220 has a window 221 in line with which is disposed a lens 222 for projecting to infinity the light rays generated by the combustion of the hydrogen in the air.

In the light beam produced by lens 222 is placed a chopper formed by a rotary disk 223 having in an annular zone passing in the axis of the lens, a succession of optical filters 224 respectively appropriate to the characteristic spectrum of the desired elements. This disk 223 is driven at constant speed by an electric motor 225.

In said annular zone, filters 224 are separated by opaque zones 226 (visible in FIG. 7) one of which at least has the surface of a filter and serves for obtaining a reference signal representative of a zero light intensity, and by reflector elements 227 which reflect the light beam in the plane of disk 223 onto an optical system comprising an ultraviolet filter 228, a focusing lens 229 and an ultraviolet radiation detector 230.

Furthermore, in the axis of lens 222 is disposed an optical unit including, on the side of disk 223 opposite said lens 222 a focusing lens 231 and, substantially at the focal point of this lens 231, an optoelectronic sensor 232 responsive in the range of frequency spectra corresponding to the desired elements. Furthermore, on each side of lens 231 grids 233 are disposed made from an electrically conducting material serving as electrostatic filters. The infrared radiation may be stopped by using a dichroic filter or by metallization of lens 231, also serving as an electrostatic filter. Thus, the light beam emitted by the burner will be chopped by the opaque zones 226 of disk 223 which will only let pass in the direction of sensor 232 a cyclic succession of spectral lines in relation with the desired elements in the direction of sensor 230 and a succession of ultraviolet wave trains representative of the emission of the OH radicals of the flame, i.e. of the state of combustion inside the burner.

Advantageously, for each of the emission spectra corresponding to a desired element, the disk will comprise two successive filters, one for detecting the top of the spectrum, whereas the other is for detecting the foot of this spectrum. The subsequent subtraction of the signals emitted by these two filters will make it possible to eliminate parasite light radiations.

Figure 4:
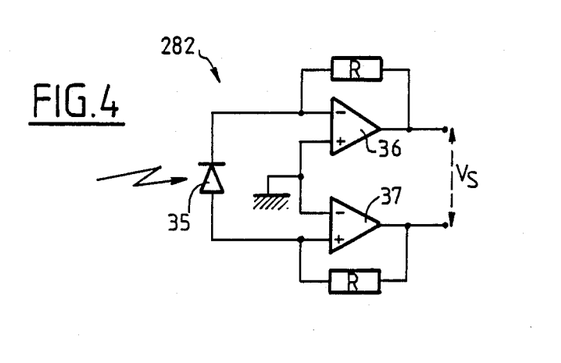
FIG. 4 shows a preferred embodiment of a detection circuit using a photodiode placed in the focusing zone of the focusing optics.

The sensor 232 may be formed of a photodiode 35 associated with a high signal/noise ratio amplifier, preferably of the type shown in FIG. 4. In this amplifier, the photodiode 35 is connected to the two inverting inputs of two respective operational amplifiers 36, 37 whose forward inputs are connected to ground. Furthermore, the inverting input of each of these amplifiers is connected to its output through a resistor R.

With this circuit, an output signal Vs is obtained between the two outputs of the two amplifiers 36, 37 equal to twice the product of the resistor R multiplied by the current Iph generated by the diode.

The noise signal will then be very much less than that of a conventional circuit which only uses a single operational amplifier.

Figure 7:
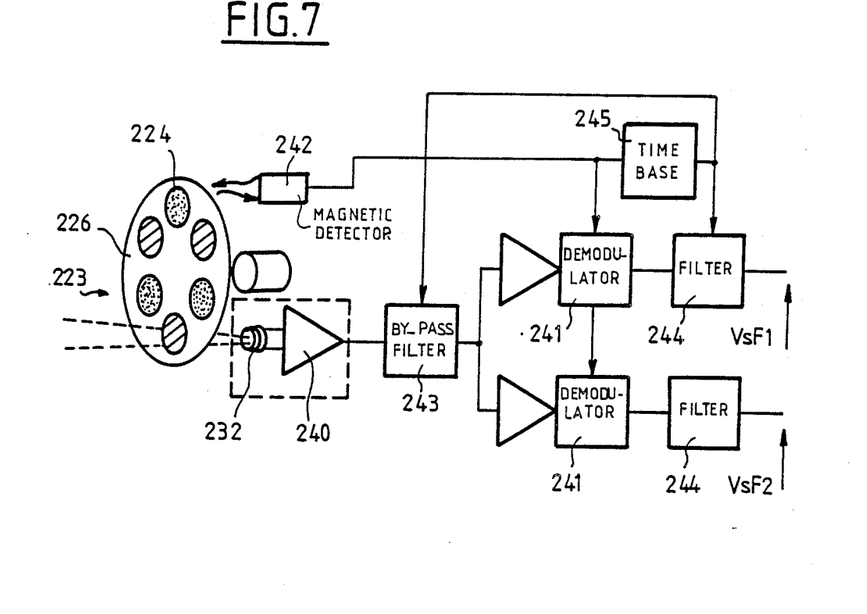
FIG. 7 is a schematical representation of the optoelectronic unit associated with the burner.

As can be seen in FIG. 7, the sensor 232 is connected by its output to a preamplifier 240 whose output signals are directed respectively to a plurality of demodulator-separators 241 driven by a synchronization signal emitted by an optical or magnetic detector 242 associated with disk 223, this circuit being designed so that each demodulator 241 only processes the signal corresponding to a given spectrum, and consequently, to a given filter 224 or a type of filters of disk 223. Advantageously, the circuit connecting the preamplifier 240 to the demodulators 241 includes a band pass filter 243 driven by the synchronisation signal, this band pass filter 243 being provided for reducing the noise of the signal applied to the demodulators 241. Similarly, the signals delivered by demodulators 241 are filtered by low pass filters 244 also driven by the synchronization signal.

These filters 244 are then connected to the converter 20 shown in FIG. 1 whose output is connected to the display unit 19.

It should be noted that for optimizing the noise level, the signal from sensor 232 must be narrowly filtered at frequencies fixed by the rotational speed of disk 223.

Such filtering causes a phase shift of the measurement signals with respect to the synchronization signals.

To attenuate this phenomenon, the position of the synchronization detector 242 must be offset angularly. However, the variations of the rotational speed of disk 223 caused for example by movements of the apparatus generate fluctuations of the phase shift and so appreciable measurement errors, the light intensity measurements no longer being made strictly at the time at which filters 224 pass in front of the optics.

To overcome this drawback, the invention proposes using filters applying the technique of capacitive chopping which makes it possible to make their breaking frequency dependent on that of a time base 245, this latter being formed by a VCO/frequency divider loop synchronized with the rotational speed of disk 223.

As mentioned above, the combustion of the hydrogen inside the burner must be begun and maintained by means of an ignition device. This ignition may be obtained by thermal catalysis by means of a platinum wire playing the role of heating resistance fed with electric current by a switching device driven by the ultraviolet radiation detector so as to be used only when it is necessary. Furthermore, for saving energy the electric power applied to this platinum wire may be limited to a minimum because of the regulation device shown in FIG. 8.

Figure 8:
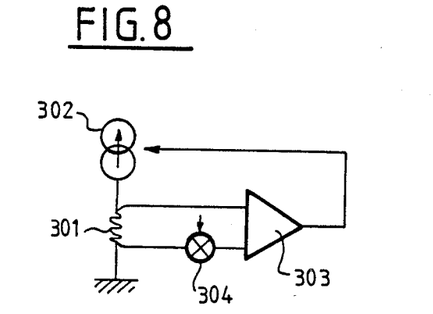
FIG. 8 shows schematically one embodiment of the burner ignition circuit.

In this device, the platinum wire 301 is fed by a current generator 302 of VCI type driven by a difference signal between the value of the resistance of the platinum wire measured at its terminals and a reference value. In this example, this difference value is delivered by an operational amplifier 303 whose two inputs are connected to the terminals of the platinum wire and one of the terminals of which further receives the reference signal through an adder 304. With this circuit, in particular, only the current is caused to flow through the platinum wire which is just necessary for producing ignition whatever the environmental conditions.

Of course, the invention is not limited to this type of ignition device alone; it could also be formed by a device generating an electric arc in the burner.

Figure 9:
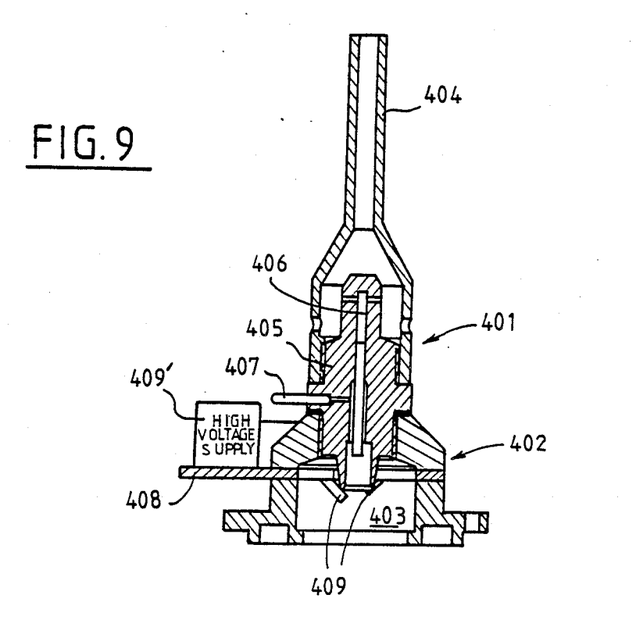
FIG. 9 is an axial section of the burner in a particularly advantageous embodiment of the invention.

Thus, in the embodiment shown in FIG. 9, the burner comprises a cylindrical body made of two parts 401, 402 assembled together, namely an intake part 401 and a part 402 defining the combustion chamber 403 at least partially.

The intake part 401 is extended on one side by a nozzle 404 for taking the air to be analysed, which may be connected to a circulator and contains, on the other side, a needle 405 with an axial injection passage 406 communicating with said nozzle 404 and into which opens the hydrogen intake circuit 407 supplied by the flow regulator. The end of needle 405 opposite nozzle 404 projects slightly inside the combustion chamber 403 and has a cavity serving both as mixing chamber and ignition chamber for the hydrogen and air mixture.

Sealing at the junction of the two parts 401, 402 of the burner is provided by a printed circuit element 408, partially in the form of a ring, which carries two ignition electrodes 409 which extend inside the combustion chamber 403 and which are connected to a high voltage supply circuit 409' carried by a portion of the element situated outside the burner.

Figure 10:
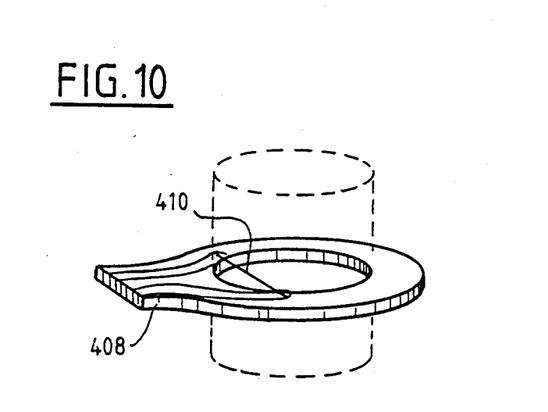
FIG. 10 is a schematical perspective view of a thermocatalysis ignition means usable in the burner shown in FIG. 9.

A structure similar to that previously described may be advantageously used in the case of thermocatalysis ignition. In this case, it is possible to use, as shown in FIG. 10, instead of electrodes 409, a platinum wire 410 which extends in the circular space defined by the element 408. Similarly, the circuit for supplying this platinum wire with power may be at least partially carried by the part of the element external to the burner.

Figure 11:
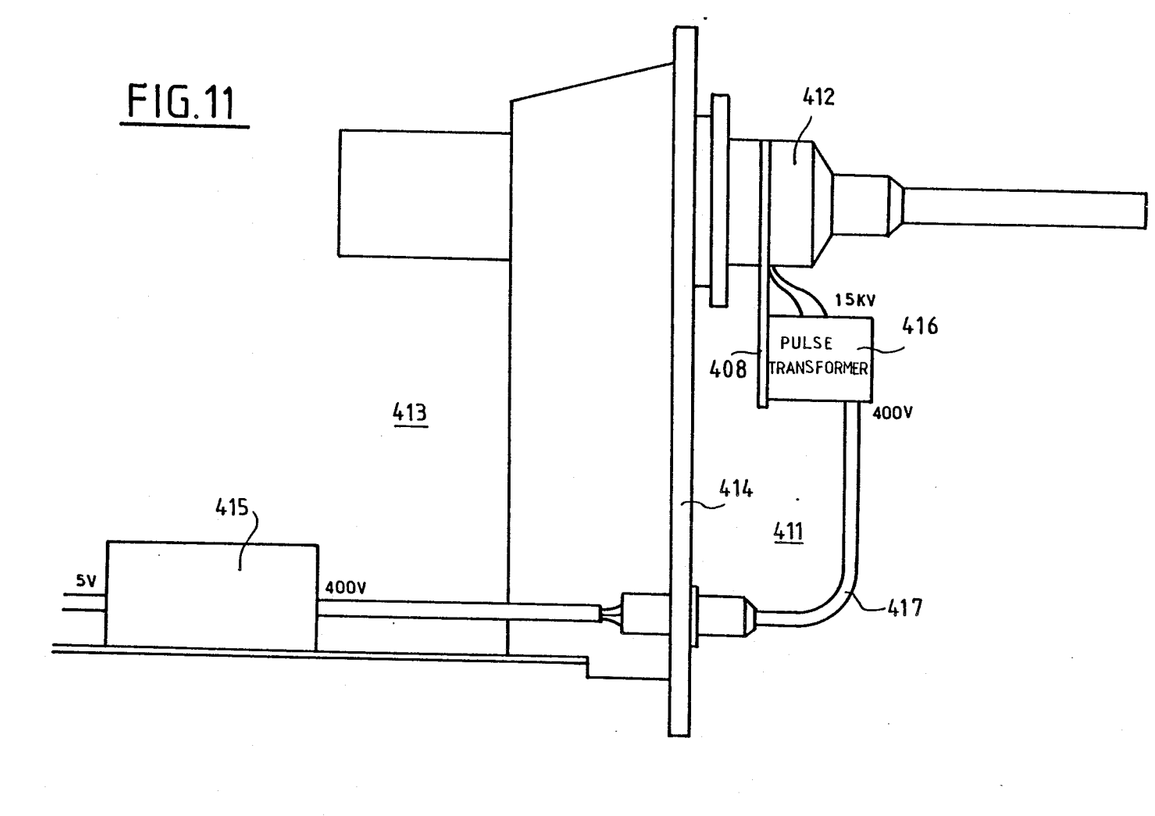
FIG. 11 shows one method of implanting electric circuits associated with an electric arc ignition means usable in the burner shown in FIG. 9.

FIG. 11 shows one implantation method particularly appropriate to the ignition of a gaseous mixture by an electric arc.

In this example, zone 411 containing burner 412 is isolated from zone 413 containing the electric measuring circuits and the optoelectronic sensors by a wall 414 made from an electrically conducting material forming a screen. The supply for the ignition device is then provided by a medium voltage booster transformer 415 situated in zone 413 this transformer 415 being connected to a very high voltage pulse transformer 416 mounted, in zone 411, on a part of the element 408 external to the burner. The connection between the medium voltage transformer 415 and transformer 416 is provided by a cable 417, preferably screened, passing through the wall 414. This arrangement in particular avoids the disturbances which the pulses generated by transformer 416 might cause on the electronic or optoelectronic measuring circuits. Another advantage of this arrangement consists in that it avoids the use of very high voltage electric connections as well as connectors appropriate for these voltages.

We claim:

1. A portable self-contained apparatus for the analysis of a gaseous composition by flame spectrophotometry, this apparatus consequently comprising inside a case fitted with a gripping member, means for carrying out a spectrographic analysis of a light radiation produced by a flame of a gaseous mixture including elements to be analysed and, in particular a flame obtained by the combustion, inside a burner of a constant flow rate hydrogen stream in a flow of air to be analyzed, said hydrogen stream being obtained by a removable hydrogen generator and said burner having a window in the axis of which said means for carrying out a spectrophotometry analysis are disposed which comprise successively:
   (i) an optical system for focusing in a focusing zone the light radiation emitted by the flame which is developed inside the burner,
   (ii) a chopper including a plurality of optical filters at the rate of at least one per characteristic spectral line of each of the said elements, as well as means for placing said filters successively in the previously focused light radiation,
   (iii) an optoelectronic cell placed in the focusing zone of the optical system,
   (iv) a demodulating circuit connected to the cell and comprising for each spectral line and, consequently, for each of said filters, a demodulator-separator driven in synchronism with the chopper so as to be made active only when the light radiation from the optical system passes through a corresponding filter, and
   (v) means for amplifying and displaying the electric signal delivered by said demodulator-separators.

2. The apparatus as claimed in claim 1, which comprises, for each spectral line corresponding to one of said elements, two successive filters, one detecting the foot of this line and the other for detecting the top of this line.

3. The apparatus as claimed in claim 1, wherein said hydrogen generator consists of a hydrogen accumulator of the type in which the release of hydrogen is obtained by heating of elements such as lanthanum-nickel granulates impregnated with hydrogen and contained in an interchangeable cartridge of small volume.

4. The apparatus as claimed in claim 3, wherein said hydrogen accumulator comprises a body of tubular shape having a plurality of radial fins which extend axially in the inner volume of the body containing the lanthanum-nickel.

5. The apparatus as claimed in claim 4, wherein said body comprises a bottom having a stopper which is ejected when the hydrogen pressure inside the body rises above the given threshold.

6. The apparatus as claimed in claim 3, further comprising servo-control means for making the heating power of the hydrogen accumulator dependent on the hydrogen pressure reigning upstream of a regulator provided for supplying the burner with hydrogen at a constant rate.

7. The apparatus as claimed in claim 5, wherein said hydrogen generator comprises heating means consisting of active components having a heating power controlled by a control voltage.

8. The apparatus as claimed in claim 6, which comprises upstream of the regulator, a hydrogen circuit which forms a buffer volume in which the hydrogen pressure may vary above a threshold value in a pressure range appropriate to that required by the regulator so as to maintain the hydrogen flow constant, said servo-control means being adapted for maintaining the hydrogen pressure reigning inside said buffer volume within said pressure range by continuously or discontinuously adjusting the electric power applied to the heating device of said accumulator.

9. The apparatus as claimed in claim 8, wherein said regulator comprises in series a membrane pressure reducer and a flow regulator.

10. The apparatus as claimed in claim 9, wherein the hydrogen pressure reigning in said buffer volume is detected by means of a detector detecting the position of the membrane of the pressure reducer.

11. The apparatus as claimed in claim 10, wherein said flow regulator comprises a hollow, preferably cylindrical, body with two opposite coaxial orifices, namely an access orifice for connecting to the hydrogen generator and an outlet orifice connected to the burner and an internal dividing wall perpendicular to the axis of said orifice, which defines two chambers inside the body, one of which, situated on the access orifice side, forms the chamber of the pressure reducer and the other, situated on the outlet orifice side, forms the chamber of the flow regulator, communication between these two chambers taking place through a bore provided in the dividing wall coaxially to said orifices.

12. The apparatus as claimed in claim 11, wherein the said access orifice is equipped with a needle having an axial channel and whose head which projects inside the chamber of the flow regulator, cooperates with a valve carried by a support structure secured to a resiliently deformable membrane which is sealingly mounted on the body and on the needle and extends in a plane perpendicular to the axis of said orifices and divides the chamber of the flow regulator into two cavities hermetically isolated from each other and the first of which communicates with the atmosphere and the second, fed with hydrogen through the channel of the needle communicates with the chamber of the flow regulator through the bore in said dividing wall.

13. The apparatus as claimed in claim 12, wherein a sealing surface forming part of the membrane cooperates with a sealing surface provided about the bore so as to close this bore when the pressure in the second cavity drops below a predetermined threshold.

14. The apparatus as claimed in claim 12, wherein said outlet orifice is equipped with a needle having an axial channel whose head cooperates with a valve carried by a resiliently deformable membrane which divides the regulation chamber into two cavities hermetically isolated from each other, one of which communicates with the central bore in said dividing wall and the other communicates with the channel of the outlet needle, and communication between these two cavities is then provided by a vacuum producing element preferably formed by a capillary passing through the membrane and one part at least of which extends radially into one of the two cavities.

15. The apparatus as claimed in claim 14, wherein the axial position of said needles is adjustable by screwing.

16. The apparatus as claimed in claim 1, wherein said filters are carried by a rotary disk further comprising an ultraviolet filter associated with a corresponding optoelectronic cell intended to supply a signal representative of the presence and of the light intensity of the flame.

17. The apparatus as claimed in claim 16, wherein said ultraviolet filter is associated with a reflector for reflecting the ultraviolet radiation in the plane of the disk.

18. The apparatus as claimed in claim 16, which further comprises a device for igniting the flame driven by said signal.

19. The apparatus as claimed in claim 18, wherein said ignition device operates by thermocatalisis.

20. The apparatus as claimed in claim 18, wherein said ignition device comprises means for generating an electric arc inside the burner.

21. The apparatus as claimed in claim 1, wherein the chopper comprises, between said optical filters, at least one opaque region having the surface of a filter, this region serving for obtaining a reference signal representative of a zero light intensity.

22. The apparatus as claimed in claim 1, wherein said optical system includes at least one lens interposed between two grids made from an electrically conducting material serving as electrostatic screen.

23. The apparatus as claimed in claim 22, wherein said optical system includes a dichroic filter or a metallization of the lens for stopping infrared radiations and achieving said electrostatic screening.

24. The apparatus as claimed in claim 1, wherein said optoelectronic cell consists of a photodiode connected to the inverting inputs of two respective operational amplifiers of a detecting circuit whose forward inputs are connected to ground, and the inverting inputs of each of these amplifiers are connected to their output by means of a resistor, and the voltage between the two output terminals of said amplifiers being used as output signal of said detecting circuit.

25. The apparatus as claimed in claim 1, wherein the burner comprises a cylindrical body made of two parts assembled together, with, at the junction between these two parts, a printed circuit element in the form of a ring having ignition means which extend inside the combustion chamber of the burner.

26. The apparatus as claimed in claim 25, wherein said printed circuit element carries at least one part of a supply circuit for said ignition means.

27. The apparatus as claimed in claim 25, wherein said ignition means consist of a platinum wire which extends into the circular space defined by said printed circuit element.

28. The apparatus as claimed in claim 25, wherein said ignition means consist of at least one electrode which extends inside the combustion chamber and in that at least a part of the burner containing said ignition means is situated in a zone isolated electrically from the measuring circuits by an electrically conducting wall.

29. The apparatus as claimed in claim 28, wherein said electrode is connected to a supply circuit comprising a high voltage pulse transformer situated in said zone, preferably on a part of said printed circuit element external to the burner, and low and medium voltage circuits which are isolated from said zone by said wall.

30. The apparatus as claimed in claim 1, wherein the flow of air inside the burner is provided by a circulator controlled as a function of the intensity of the ultraviolet radiation emitted by combustion of the hydrogen.

31. The apparatus as claimed in claim 30, which further comprises a detector for detecting malfunctions and means for interrupting the ignition means when this detector delivers a fault signal.

32. The apparatus as claimed in claim 16, wherein said demodulator-separator are driven by a synchronization signal emitted by an optical or magnetic detector associated with the rotary disk so that each demodulator only processes the signal corresponding to a given filter of the disk.

33. The apparatus as claimed in claim 32, wherein the signal delivered by said optoelectronic cell are filtered by means of at least one filter driven by said synchronization signal.

34. The apparatus as claimed in claim 33, wherein said filter comprises capacitive chopping means whose breaking frequency is slaved to that of a time base synchronized with the rotational speed of the disk.

35. The apparatus as claimed in claim 1, wherein said display means include a signalling system emitting a light or sound signal with variable amplitude and/or frequency.

* * * * *